US 11,779,291 B2

(12) United States Patent
Klima et al.

(10) Patent No.: US 11,779,291 B2
(45) Date of Patent: Oct. 10, 2023

(54) INTERFACE MODULE FOR X-RAY COLLIMATOR

(71) Applicant: Siemens Healthcare GmbH, Erlangen (DE)

(72) Inventors: Philipp Klima, Oesdorf (DE); Stefan Popp, Wiesenttal (DE); Philipp Hirmer, Mantel (DE); Christoph Loetzsch, Pautzfeld (DE); Stefan Kick, Schirmitz (DE); Johannes Rieger, Bayreuth (DE); Albert Hutterer, Wetterfeld (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 2 days.

(21) Appl. No.: 17/705,661

(22) Filed: Mar. 28, 2022

(65) Prior Publication Data
US 2022/0319732 A1 Oct. 6, 2022

(30) Foreign Application Priority Data

Mar. 31, 2021 (DE) ...................... 10 2021 203 285.0
Apr. 15, 2021 (DE) ...................... 10 2021 203 754.2

(51) Int. Cl.
*A61B 6/06* (2006.01)
*G21K 1/04* (2006.01)
*H05G 1/02* (2006.01)

(52) U.S. Cl.
CPC .................. *A61B 6/06* (2013.01); *G21K 1/04* (2013.01); *H05G 1/02* (2013.01)

(58) Field of Classification Search
None
See application file for complete search history.

(56) References Cited

U.S. PATENT DOCUMENTS

| 4,246,488 A * | 1/1981 | Hura | G21K 1/10 |
| | | | 378/151 |
| 7,092,489 B2 * | 8/2006 | Li | G21K 1/02 |
| | | | 403/338 |
| 7,397,899 B2 * | 7/2008 | Li | G21K 1/02 |
| | | | 378/205 |

(Continued)

FOREIGN PATENT DOCUMENTS

| CN | 201790819 U | * | 4/2011 | |
| CN | 1786818 B | * | 6/2011 | ............... G21K 1/02 |

(Continued)

OTHER PUBLICATIONS

German Decision to Grant and English translation thereof dated Oct. 19, 2022.

*Primary Examiner* — Thomas R Artman
(74) *Attorney, Agent, or Firm* — Harness, Dickey & Pierce, P.L.C.

(57) ABSTRACT

An interface module to connect a collimator to an X-ray generator, includes: a base plate, which forms a support area for an X-ray tube unit flange of the X-ray generator; an adjustment plate, which is rotatably connected to the base plate; and at least one swivel element movably connected to the base plate and adjustment plate such that, upon rotation of the adjustment plate, the at least one swivel element pivots between a clamping position and an open position.

20 Claims, 7 Drawing Sheets

(56) References Cited

U.S. PATENT DOCUMENTS

| | | | | |
|---|---|---|---|---|
| 8,699,669 | B2* | 4/2014 | Yuan | G21K 1/02 |
| | | | | 378/147 |
| 9,892,810 | B2* | 2/2018 | Kwerreveld | G21F 1/085 |
| 11,497,460 | B2* | 11/2022 | Hutterer | A61B 6/58 |
| 2006/0126791 | A1* | 6/2006 | Li | G21K 1/02 |
| | | | | 378/147 |
| 2006/0126792 | A1* | 6/2006 | Li | G21K 1/02 |
| | | | | 378/147 |
| 2012/0134476 | A1* | 5/2012 | Yuan | G21K 1/02 |
| | | | | 378/147 |
| 2017/0256329 | A1* | 9/2017 | Kwerreveld | G21K 1/04 |
| 2021/0315536 | A1 | 10/2021 | Hutterer et al. | |
| 2022/0319732 | A1* | 10/2022 | Klima | G21K 1/04 |

FOREIGN PATENT DOCUMENTS

| | | | | |
|---|---|---|---|---|
| CN | 104225805 | A | | 12/2014 |
| CN | 105559812 | A | | 5/2016 |
| CN | 210919662 | U | * | 7/2020 |
| DE | 202019106995 | U1 | | 1/2020 |
| DE | 102020204673 | A1 | | 10/2021 |

* cited by examiner

FIG 13

INTERFACE MODULE FOR X-RAY COLLIMATOR

CROSS-REFERENCE TO RELATED APPLICATION(S)

The present application claims priority under 35 U.S.C. § 119 to German Patent Application Nos. DE 102021203285.0, filed Mar. 31, 2021, and DE 102021203754.2, filed Apr. 15, 2021, the entire contents of each of which are incorporated herein by reference.

FIELD

Embodiments of this application relate to an interface module for connecting an X-ray collimator to an X-ray generator. The interface module comprises at least one swivel element for the simple attachment of the X-ray collimator to the X-ray generator.

BACKGROUND

One of the uses of an X-ray collimator, referred to below for the sake of simplicity as a collimator, in traditional radiography using X-ray radiation is to adjust the X-ray radiation generated and emitted by an X-ray generator to a desired image area. The patient to be examined or the patient's body part to be examined is arranged in the image area. For collimation of the X-ray radiation the collimator is installed in the direction in which the X-ray radiation is emitted to the X-ray generator. As a result, the collimator is penetrated by the X-ray radiation, so that it passes a variable, adjustable collimation window of the collimator, said window adjusting the X-ray beam to the desired image area.

The collimation of the X-ray radiation can on the one hand take place in that the collimator is rotated relative to the X-ray generator about an axis perpendicular to the outlet area of the X-ray radiation. As a result, an orientation or an angular position of the collimation window is adapted to the X-ray generator or the X-ray beam, in order for example to be better able to take into account distinctive anatomical features of the patient or the patient's position on a patient table. On the other hand the collimator can comprise at least one diaphragm, preferably multiple diaphragms, the position or location of which relative to a collimator housing or to the X-ray radiation can be adapted in order to change the size and/or shape of the collimation window. In this way the image area is also adapted. This procedure serves in particular to reduce the patient's exposure to radiation.

SUMMARY

In known solutions the collimator is attached to an X-ray generator so that it is suspended therefrom or rests thereon. For this purpose the collimator comprises an interface module on its side facing the X-ray generator, into which a flange of the X-ray generator (X-ray tube unit flange) engages or can be inserted. The rotatability of the collimator about the axis perpendicular to the outlet area (vertical axis) is achieved by way of the interface module. For installation the collimator or the interface module is only accessible from the side.

In the case of suspended installation the collimator is pressed and held with the interface module from below onto the X-ray generator or the flange thereof. At the same time, for example, three threaded pins offset by 120° must each be screwed into a self-locking thread of the interface module manually using an appropriate tool. This means that three sliders are moved successively over a collar of the X-ray tube unit flange. Only when the third slider has been screwed in does the interface module develop a sufficient clamping effect that is secure in the vertical direction. Only now can the collimator be released. Thus with a collimator weighing 10 kg-12 kg a considerable amount of force is required for the installation over an extended period of time.

In contrast, embodiments of the present invention provide an alternative manner to enable a collimator to be installed on an X-ray generator quickly, simply and in particular without the use of tools. In particular, embodiments of the present invention may reliably prevent errors during the installation.

Embodiments provide a novel interface module and a collimator.

A first aspect of embodiments of the present invention focuses on an interface module for connecting a collimator to an X-ray generator.

The interface module comprises a base plate, which forms a support area for an X-ray tube unit flange, in particular the collar of the X-ray tube unit flange of an X-ray generator. The support area serves as a contact surface or defines the position of the X-ray tube unit flange relative to the collimator in the installed state. In this state the support area and collar of the X-ray tube unit flange touch one another.

The interface module further comprises an adjustment plate, which is rotatably connected to the base plate. The interface module is further characterized by at least one swivel element which is movably connected to the base plate and the adjustment plate. The swivel element is connected to the base plate and the adjustment plate such that upon rotation of the adjustment plate it pivots between a clamping position and an open position.

The base plate and the adjustment plate are flat structures which extend far less in one spatial dimension than in the other two spatial dimensions. They are furthermore arranged relative to one another such that their base areas largely overlap or cover one another. In some embodiments their area center points or their area mid-points lie on a common axis perpendicular to their base areas or, in the installed state of a collimator comprising an interface module, perpendicular to the area of the outlet window for the X-ray radiation in the X-ray tube unit flange.

In some embodiments, the adjustment plate is arranged above the base plate in respect of the collimator, in other words further away from a collimator housing.

The base plate in some embodiments is firmly connected to the collimator housing, preferably screwed via multiple screw points. Alternatively the connection can be created by rivets, a press connection or a bonded connection. In alternative embodiments the base plate can also be formed integrally with, for example, a support structure of the collimator, for example as a cast component.

In some embodiments, the adjustment plate and the base plate preferably each comprise an outlet opening for X-ray radiation. In other words the interface module, in particular the base plate and the adjustment plate, can in some embodiments be penetrated by the X-ray radiation emitted by the X-ray generator through the X-ray tube unit flange. The outlet opening is in each case preferably arranged in the center of the base plate or adjustment plate and comprises the respective area mid-point. Particularly preferably, the area mid-points overlap with the center points of the outlet openings. The outlet openings are preferably therefore likewise aligned to one another. Other configurations are however possible. In some embodiments the center points of the outlet openings each lie on the same axis as the area mid-points.

The base areas and the outlet openings of the base plate and the adjustment plate are preferably embodied as round/circular or as substantially round/circular. the present invention is not however restricted to this.

In some embodiments, the external diameter is 15 cm to 23 cm, preferably 18 cm to 21 cm, in particular 19.2 cm.

In some embodiments, the diameter of the outlet opening of the base plate is 8 cm to 14 cm, preferably 9 cm to 13 cm, in particular 11 cm. In some embodiments the diameter of the outlet opening of the adjustment plate is 11 cm to 19 cm, preferably 13 cm to 18 cm, in particular 14 cm to 16 cm, for example 15 cm.

To receive the X-ray tube unit flange, in particular to receive the collar thereof, the base plate forms a support area. The support area is aligned in the direction of the X-ray generator or X-ray tube unit flange. The support area preferably has a base area which is embodied to receive the X-ray tube unit flange or the flange collar. The receiving area therefore preferably has the same base area as the collar of the X-ray tube unit flange; in particular it is embodied as somewhat larger, in order to facilitate the introduction of the X-ray tube unit flange onto the support area. The support area preferably surrounds the outlet opening of the base plate; in particular the support area is a closed area, particularly preferably an area closed around the outlet opening. In other words the support area encloses the outlet opening. In this respect the support area is embodied as annular in some embodiments, in other words with a defined external and internal diameter. In some embodiments the support area is formed by a recess or depression with a height of 1.5 cm to 3.5 mm, preferably 2 mm to 2.5 mm, in particular 2.1 mm of the base area of the base plate facing the X-ray tube unit flange. This advantageously brings about a stabilization of the position of the X-ray tube unit flange in the interface module.

The outlet opening of the base plate is smaller in some embodiments than that of the adjustment plate. The outlet opening of the adjustment plate is preferably embodied to receive the X-ray tube unit flange, in particular the collar thereof. It therefore preferably has at least the same base area as the X-ray tube unit flange, and is preferably somewhat larger, in order to facilitate the insertion of the X-ray tube unit flange into the interface module.

In some embodiments, the adjustment plate is embodied so as to be rotatable about an axis through its area mid-point, preferably also the center point of its outlet opening, relative to the base plate. This means the adjustment plate is embodied such that it can change its angular position in respect of the base plate. In this case the adjustment plate is coupled to the base plate, i.e. the adjustment plate is connected by a coupling mechanism to the base plate and via it to the collimator housing. The coupling mechanism in this case limits the rotary motion in some embodiments of the present invention. In particular, the rotary motion is limited by the coupling mechanism to a defined angular increment of 25°.

The at least one swivel element is likewise a flat structure which extends considerably less in one spatial dimension compared to the other two spatial dimensions. The swivel element has the shape of a lever or wing in some embodiments. The swivel element has smaller dimensions compared to the external dimensions of the base plate and the adjustment plate.

In some embodiments, the swivel element has a length of 80 mm to 100 mm, preferably 90 mm and a width of 30 mm to 40 mm, preferably 35 mm.

In some embodiments, the at least one swivel element is arranged between the base plate and the adjustment plate. In other embodiments, it can for example also be arranged above the adjustment plate, i.e. closer to the X-ray generator in the installed state of the interface module. The at least one swivel element is connected to the base plate and the adjustment plate and as soon as the adjustment plate completes a rotary motion pivots between a clamping position and an open position. In accordance with embodiments of the present invention, multiple clamping positions can be provided, as is explained in greater detail below.

In some embodiments of the present invention, the swivel element is arranged in the open position outside the support area for the X-ray tube unit flange formed by the base area. In a plan view, for example viewed from above or from the direction of the X-ray generator, the base area of the swivel element lies in the open position completely outside the outlet opening of the adjustment plate. The support area of the base plate is therefore completely exposed. The interface module is open in the open position of the swivel element to enable the X-ray tube unit flange to be received or removed.

In some embodiments of the present invention, the swivel element is arranged in the clamping position such that it projects at least partially over the support area. In a plan view, for example viewed from above or from the direction of the X-ray generator, the base area of the swivel element lies in the open position at least partially inside the outlet opening of the adjustment plate. The swivel element therefore partially projects over or covers the support area of the base plate. The support area is no longer fully exposed. The interface module is obstructed in the clamping position of the swivel element, and cannot receive the X-ray tube unit flange. If the swivel element arrives at the clamping position by rotation of the adjustment plate, when the X-ray tube unit flange is inserted into the interface module, the X-ray tube unit flange can no longer be removed from the interface module after the clamping position is reached. More precisely, the swivel element covers the collar of the X-ray tube unit flange and holds it on the support area. In the clamping position the swivel element in this respect causes the interface module to be secured or attached to the X-ray tube unit flange. The collar of the X-ray tube unit flange is clamped between the support area of the base plate and the swivel element and in this manner is fixed.

By coupling or connecting the swivel element to the adjustment plate and the base plate an adjustment movement of the swivel element into the clamping position can only be brought about according to the present invention by rotating the adjustment plate in order to close the interface module. This enables a collimator to be installed on an X-ray tube unit flange in an advantageously fast manner.

In an embodiment of the present invention, the interface module comprises multiple, namely three, swivel elements, in particular embodied identically as described above. These are in particular arranged at an angular spacing of 120° around the support area of the base plate. In this embodiment the base plate and adjustment plate and the outlet openings thereof are preferably embodied as circular. Each of the swivel elements is now movably/adjustably connected to the base plate and the adjustment plate and is in each case adjusted by a rotary motion of the adjustment plate between the open position and the clamping position. The movements of the swivel elements are advantageously coupled to one another via the adjustment plate and said coupling mechanism. Thanks to an evenly distributed arrangement of multiple swivel elements around the outlet opening of the adjustment plate or the support area of the base plate, an in particular uniform clamping effect onto the collar of the X-ray tube unit flange can advantageously be brought about very quickly on closure of the interface module. An incorrect installation caused by the collimator being tilted or inclined in respect of the X-ray generator during the installation can be advantageously averted in this manner.

In other, alternative embodiments of the present invention, two or more than three clamping elements, for example four, five or even six, can be included in a uniformly distributed arrangement.

In further embodiments of the present invention, the adjustment plate comprises an adjustment lever, which when actuated causes the adjustment plate to rotate. In this embodiment, a manual actuation of the adjustment plate is enabled thanks to the adjustment lever of the adjustment plate. The adjustment lever is preferably arranged on the adjustment plate such that it can be readily accessed manually by an installer when the collimator is being held on the X-ray generator for installation. In some embodiments, the adjustment lever is integrally connected to the adjustment plate. In some embodiments, the adjustment lever projects in a planar manner out from the base area of the adjustment plate. The adjustment lever can for example have a length and a width of 18 mm by 18 mm. For better accessibility it in particular advantageously protrudes out of a housing/casing of the interface module. Any other embodiments for the adjustment lever are likewise conceivable.

Because an adjustment lever is provided for manual actuation of the adjustment plate it is advantageously possible to dispense with the use of a tool during installation.

In an alternative embodiment of the present invention, the adjustment plate comprises a motorized drive, in order to rotate the adjustment plate. An actuation element can further be provided, which is connected to the motorized drive and which on actuation brings about an activation of the motorized drive. The motorized drive is further connected to the adjustment plate and on activation transmits a drive force to the adjustment plate, as a result of which the latter is rotated. In some embodiments, two actuation elements can be provided in each case for a rotary motion with an opposite direction of rotation, for example in the form of two push-buttons. Alternatively, an actuation element with two actuation positions corresponding to the opposite directions of rotation can be embodied, for example as a rocker switch or slide controller. The at least one actuation element can preferably be arranged on an external side of the interface module housing or the casing thereof—readily accessible by an installer during installation. The installation of the collimator is in this manner further simplified in the event of increased component complexity.

In one embodiment of the present invention, the swivel element is pivotably connected to the base plate via at least one first and at least one second coupling element, each firmly connected to the base plate, wherein the second coupling element engages in a first slot in the swivel element to guide the pivoting motion. No relative movement is therefore possible between the base plate and the first and second coupling element.

In some embodiments, the first coupling element penetrates a borehole in the base plate and a borehole in the at least one swivel element. In some embodiments the second coupling element penetrates a further borehole in the base plate and a further borehole in the swivel element. This further borehole in the swivel element is embodied as a first closed slot in the swivel element or a slot open on one side. In this manner a swiveling motion of the swivel element about the longitudinal axis of the first coupling element is enabled, during which swiveling motion the swivel element changes its relative position in respect of the second coupling element or the base plate such that the second coupling element moves along the slot.

In some embodiments, the first and the further borehole in the swivel element are preferably arranged close to the short sides of the swivel element, in order in this manner to form an advantageously long swivel lever.

In some embodiments, the first slot in the swivel element is in particular oriented or arranged to run substantially radially when the base plate and adjustment plate or the outlet openings are circular or round in shape.

In some embodiments of the present invention, the coupling elements can in each case comprise a screw or a bolt. The shaft of the screw/bolt is then surrounded at the height of the swivel element by a sleeve that can rotate about the shaft of the screw/bolt. The sleeve is fitted exactly into the borehole in the swivel element and thus enables a rotating or swiveling motion of the swivel element relative to the respective shaft of the screw/bolt.

In further embodiments of the present invention, the second coupling element also engages in a slot in the adjustment plate. In particular, in some embodiments with a circular or round shape of the base plate and adjustment plate or of the outlet openings, the slot in the adjustment plate is embodied as a slot running substantially in the circumferential direction. In a compact and in particular flat embodiment of the interface mode the slot forms a recess for the second coupling element and thus enables the rotary motion of the adjustment plate in respect of the base plate.

In other, alternative embodiments, the adjustment plate is embodied as narrower in the radial direction, so that the adjustment plate can move relative to or along the second coupling element without requiring any additional measures. The second coupling element here lies outside the base area of the adjustment plate. A recess in the form of a slot is advantageously unnecessary.

In further embodiments of the interface module, the adjustment plate is rotatably connected to the base plate via at least one third coupling element, wherein the third coupling element engages in a slot in the base plate to guide the rotary motion. The slot in the base plate is preferably a slot running in a circumferential direction to the base plate. The third coupling element is firmly connected to the adjustment plate, i.e. adjustment plate and third coupling element are moved jointly or together. The length of this slot in the base plate defines the angular increment about which the adjustment plate can maximally be rotated and about which the adjustment plate must be rotated in order to bring the at least one swivel element from the open position to the clamping position or vice versa.

The third coupling element can in principle be embodied like the first or second coupling element, wherein a sleeve is here fitted precisely into the slot in the base plate, in order to enable the relative motion between a third coupling element and the base plate.

Alternatively, a locating screw or a cylinder head screw with a sleeve made of steel or two sleeves that fit into one another (for example made of plastic (outer) and steel (inner)) can also be provided for the embodiment of the coupling elements, wherein the plastic is embodied as a soft or flexible material, to compensate for adverse component tolerances. In particular, a clamping effect can be further increased by pressing the plastic sleeves together and can be maintained by a securing device, as described in greater detail below.

The rotary motion of the adjustment plate in respect of the base plate is guided by the slot in the base plate. The adjustment plate can therefore adopt only the positions defined by the slot in the base plate in respect of the base plate.

In some embodiments of the present invention, the third coupling element penetrates a second slot in the swivel element at the same time as guiding the pivoting motion. In some embodiments, the second slot in the swivel element extends in the longitudinal direction of the swivel element. In some embodiments, the second slot therefore runs substantially perpendicular to the first slot in the swivel element. In some embodiments, the second slot is curved, just like the first slot in the swivel element. Thanks to the third coupling element the at least one swivel element is forced by the rotary motion of the adjustment plate guided with the help of the slot in the base plate to adopt a swiveling motion about the first coupling element and in this manner moves between the open position and the clamping position. The pivoting motion is in this case guided by the second coupling element along the first slot in the at least one pivot element.

If multiple swivel elements are provided, these are coupled to one another in their movement via the adjustment plate and the coupling elements respectively provided for each swivel element. Only by rotating the adjustment plate can they be moved back and forth simultaneously and advantageously quickly between an open position and a clamping position. Thanks to one or more embodiments of the interface module the initial installation of the collimator is not only simplified and/or accelerated, but in particular so too is a servicing cycle, if this includes disassembly/installation of the collimator.

In accordance with embodiments of the present invention, other coupling mechanisms can also be provided for the swivel elements, for example similar to a drill chuck, even though a closure of the interface module or a clamping effect can typically only be achieved less quickly.

In a further embodiment of the present invention, the interface module comprises a securing device, which is embodied to fix at least one swivel element in the clamping position. The securing device is embodied to prevent any inadvertent release of the clamping effect of the interface module. The securing device consequently locks the at least one swivel element in its clamping position, in particular by a mechanical engagement in the swivel element. In some embodiments of the present invention, the securing device is embodied to bring about the locking automatically, as soon as the at least one swivel element has adopted its clamping position, without a user or installer having to activate the securing device. In some embodiments of the present invention, the securing device is embodied such that the locking can be released again only after the active actuation of the securing device. This advantageously increases the safety of installation, as well as the safety of operation.

In further embodiments, the securing device is rotatably or bendably connected to the adjustment plate and comprises a latching hook, which under spring force adopts a latching position in a latching groove of the at least one swivel element when the swivel element adopts the clamping position.

The securing device is therefore arranged on the adjustment plate and always completes a rotary motion with the adjustment plate. However, the securing device can at least partially change a relative position in respect of the adjustment plate, for example by a rotary motion about a center of rotation attached to the adjustment plate or by distortion of at least one segment of the securing device in respect of a further segment. The securing device is arranged inside the interface module such that it, or rather its latching hook, can engage with the at least one swivel element, or rather its latching groove. The securing device and swivel element preferably lie in the same plane, for example between or above the base plate and adjustment plate. In particular, the latching hook and the latching groove are also embodied in the same plane. However, the present invention is not restricted to this.

The latching hook is acted on by spring force, i.e. it is forced by a spring force acting on it into an initial position, wherein the spring is also comprised by the securing device. The latching hook is arranged such that as soon as it comes into contact with the swivel element thanks to the rotation of the adjustment plate, it is brought out of its initial position against the spring force. If the adjustment plate is rotated further to close the interface module the securing device together with a latching hook deflected from the initial position moves past the swivel element until the latching groove of the swivel element is reached. Under spring force the latching hook latches into the latching groove and in the latching groove again adopts its initial position and thereby the latching position.

The spring of the securing device can for example be embodied as a spiral spring or as a spring steel sheet, via which the latching hook is connected to the adjustment plate. In some embodiments, the securing device itself forms the spring in a spring steel sheet-like subregion, via which at least the latching hook is connected relatively movably in respect of other subregions of the securing device fixed to the adjustment plate.

If when the adjustment plate is rotated the swivel element moves into the clamping position, the clamping area engages behind the X-ray tube unit flange collar arranged on the support area and presses it onto the support area. Thanks to the interaction of the latching groove and securing device the X-ray tube unit flange collar is now secured in this position and cannot be inadvertently removed from the outlet opening.

In further embodiments of the present invention, the at least one swivel element has a clamping area with a chamfer. The subregion of the swivel element that in the clamping position projects over the support area of the base plate or clamps the collar of the X-ray tube unit flange to the support area is known as the clamping area. In some embodiments of the present invention, the clamping area can be formed as a tag-like or leaf-like subregion which projects out from the usual shape of the swivel element and is arranged in the plane of the remainder of the swivel element, and which is aligned in the direction of the outlet opening.

The chamfer of the clamping area describes a bevel of a base area of the swivel element which at least in part faces the collar of the X-ray tube unit flange in the clamping position. The bevel therefore has an angle to the base area of the swivel element which is not equal to 90°. In an embodiment of the present invention, the collar of the X-ray tube unit flange likewise has a chamfer, in particular a chamfer of 45°. In some embodiments the clamping area likewise replicates this collar chamfer at 45°. In other words, in the clamping position both chamfered subareas of the X-ray tube unit flange collar and clamping area come into contact with one another. In alternative embodiments, a sliding element can be provided on the clamping area of the clamping element, wherein the sliding element has the chamfer described above.

In a an embodiment of the present invention, the swivel element has a plurality of latching grooves. These are preferably arranged along the displacement path of the securing device or of the latching hook. If upon rotation of the adjustment plate the swivel element moves to the clamping position, the clamping area engages behind the X-ray tube unit flange collar arranged on the support area and presses it onto the support area. The chamfered subareas are also brought into contact. Because multiple latching positions/stop locations are provided for the latching hook of the securing device and the chamfering of the clamping area and X-ray tube unit flange collar, one of a plurality of clamping strengths can now be set, similarly to a ratchet spanner or cable tie. In this manner manufacturing-related dimensional deviations in the components can be easily compensated for.

In a further embodiment of the present invention, the securing device comprises a first control notch, which lies congruent to at least one second control notch of the adjustment plate and/or of the base plate, when the latching hook adopts the latching position, that is to say when the interface module is locked in at least one clamping position by the safety device. The at least two control notches are consequently congruent or aligned to one another, when the interface module is locked. This enables a simple visual check during installation. In some embodiments, the control notch can also be color-coded, for example in red, in order to further simplify the visual check.

In a further embodiment of the present invention, the support area for the X-ray tube unit flange comprises at least one spring-loaded pressure device, which presses the X-ray tube unit flange against the swivel elements in the clamping position. The at least one pressure device brings about an opposing force to the at least one swivel element, which likewise acts on the X-ray tube unit flange. The at least one pressure device also advantageously ensures that the X-ray tube unit flange collar is stably fixed in the interface module and thus prevents any slippage or inadvertent deviation from a target position, even in the event of variations in components. In some embodiments, only one pressure device is provided in the support area, for example an elastically deformable pressure ring, which is inserted into the support area. In other embodiments, multiple pressure devices can also be provided, for example in the form of a plurality of individual pressure tabs which are spaced evenly apart from one another and in particular in the form of individually spring-loaded pressure tabs or pressure pieces.

In further embodiments of the present invention, the interface module comprises an adjustment device for fine-tuning an angular position between the collimator and the X-ray generator. The adjustment device comprises a spring-loaded pressure element which engages into a recess of the X-ray tube unit flange through the support area to define the angular position in a 0° position, further comprising an adjusting device for setting the 0° position.

The adjustment device initially serves to establish a 0° position of the collimator in respect of the X-ray generator. The 0° position describes an initial or default position of the collimator to the X-ray generator during installation, in which for example the collimator is aligned to the X-ray outlet window of the X-ray generator. In this position the collimator can be fixed by a spring-loaded pressure element. This is arranged such that it penetrates a corresponding opening in the support area and engages in a recess in the collar of the X-ray tube unit flange. The adjustment device is in this case preferably firmly connected to the base plate. Alternatively, the adjustment device can be embodied as a separate assembly which is attached at another point, for example a support structure of the collimator. The end of the pressure element that engages in the recess is preferably rounded or chamfered. By applying a defined torque to the collimator or the interface module the pressure element is pushed against the spring force out of the recess of the X-ray tube unit flange collar and enables the collimator to be moved, or rather rotated, together with the interface module in the installed state. In other words the adjustment device enables the collimator together with the interface module to be rotated with the at least one swivel element in the clamping position around the X-ray tube unit flange. In this manner any angular position between collimator and X-ray generator can be set manually.

The likewise comprised setting device further enables an adjustment of the 0° position, when this cannot be achieved precisely, for example because of manufacturing inaccuracies in the individual components. For this, the setting device for example comprises a slot running circumferentially around the base plate with an adjusting screw. By undoing the adjusting screw the angular position of the base plate can be adjusted by approximately +/−1° relative to the X-ray tube unit flange. The opening in the base plate is embodied as correspondingly large. The pressure element can in this case be rotated about its axis of rotation by approximately +/−5°.

In a further aspect, embodiments of the present invention relate to a collimator for the collimation of X-ray radiation comprising an interface module.

As already explained above, a collimator is used to collimate X-ray radiation emitted by an X-ray focal point of the X-ray generator to an X-ray detector of an X-ray imaging system. In other words the X-ray radiation which is not directed at the X-ray detector should be masked out by the collimator. This in particular prevents a person who is to be examined from being exposed to X-ray radiation that does not relate to the imaging and generally reduces exposure to radiation. To this end the collimator typically comprises a diaphragm system with at least one diaphragm. This can be formed in any way. By actuating the diaphragm system or adjusting the at least one diaphragm of the diaphragm system the X-ray radiation, in particular the extent of the X-ray beam, can be set to a desired image area. The desired image area in this case typically maximally corresponds to the X-ray-sensitive detection area of the X-ray detector, but in some embodiments can also be smaller. An example of a collimator for the collimation of X-ray radiation is described for example in German utility model DE 20 2019 106 995 U or German patent application DE 10 2020 204 673.5 A1.

Embodiments of the present invention enable a collimator to be installed on an X-ray generator simply, particularly quickly and in particular without the use of tools. Coupling multiple swivel elements uniformly arranged around the collar of the X-ray tube unit flange also brings about a uniform clamping effect onto the X-ray tube unit flange collar. The interface module in particular means that any tilting of the collimator in the event of a deflection from the 0° position of up to 90° relative to the X-ray generator is minimized. In addition, the present invention also brings about a stable relative position of the collimator to the X-ray generator, if both are jointly rotated, inclined or tilted into any angular position to a background, for example for an image data acquisition. The securing device further results in increased safety of installation and handling. Any inadvertent opening of the interface module is prevented by the securing device. The interface module makes it unnecessary to provide a separate quick-change system for the purposes of manufacturing, testing, transportation, etc., and itself forms an integrated interface.

BRIEF DESCRIPTION OF THE DRAWINGS

The properties, features and advantages of the present invention described above and the way in which they are achieved will become clearer and more readily understandable in connection with the following description of the example embodiments, which are explained in greater detail for the drawings. This description does not result in any limitation of the present invention to these example embodiments. In different figures the same components are provided with identical reference characters. The figures are in general not drawn to scale. In the drawings.

DETAILED DESCRIPTION

Figure 1:
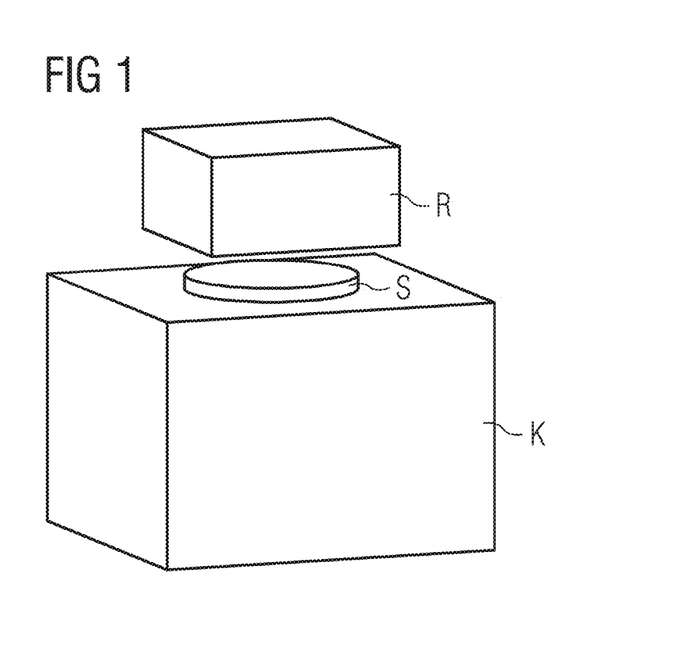
FIG. 1 shows a view of a collimator comprising an interface module for installation on an X-ray generator in an example embodiment of the present invention.

FIG. 1 shows a view of a collimator K for the collimation of X-ray radiation in an example embodiment of the present invention. The X-ray radiation is generated and emitted by an X-ray generator R, an X-ray beam source. The X-ray radiation exits through an X-ray outlet window of the X-ray generator R. The collimator K comprises an interface module S for the installation of the collimator K on the X-ray generator R. The interface module S is firmly connected to the collimator K. It is firmly screwed to the collimator housing with multiple screws. The interface module S is aligned to the X-ray outlet window of the X-ray generator R. The X-ray radiation therefore penetrates through the interface module S and then through the X-ray collimator. At least one diaphragm is provided in the interior of the collimator K, the position of which relative to the X-ray beam can be adjusted in order to collimate this.

Different forms of embodiment of the interface module S are described in greater detail below.

Figure 2:
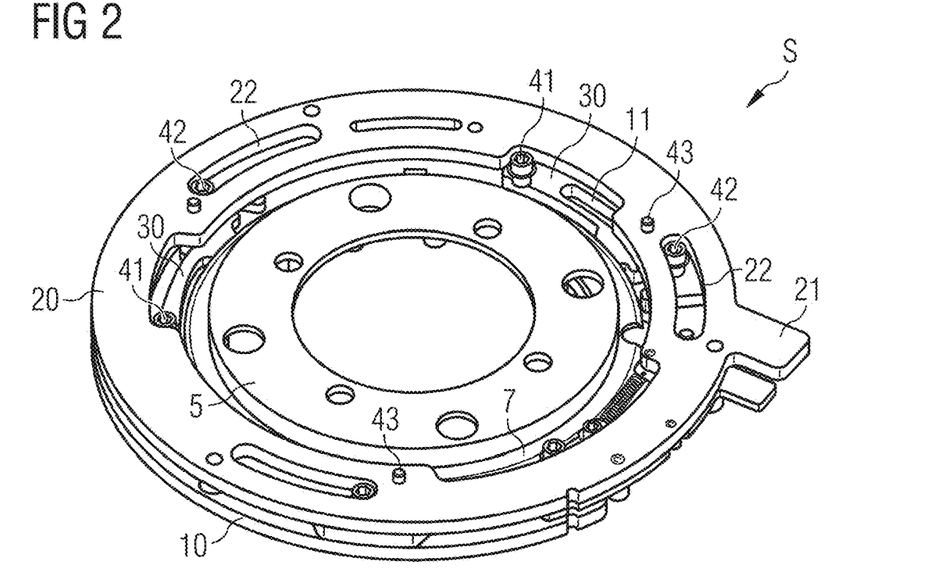
FIG. 2 shows a perspective view of a interface module in an example embodiment of the present invention.

FIG. 2 shows a perspective view of an interface module in a first example embodiment of the present invention.

Figure 3:
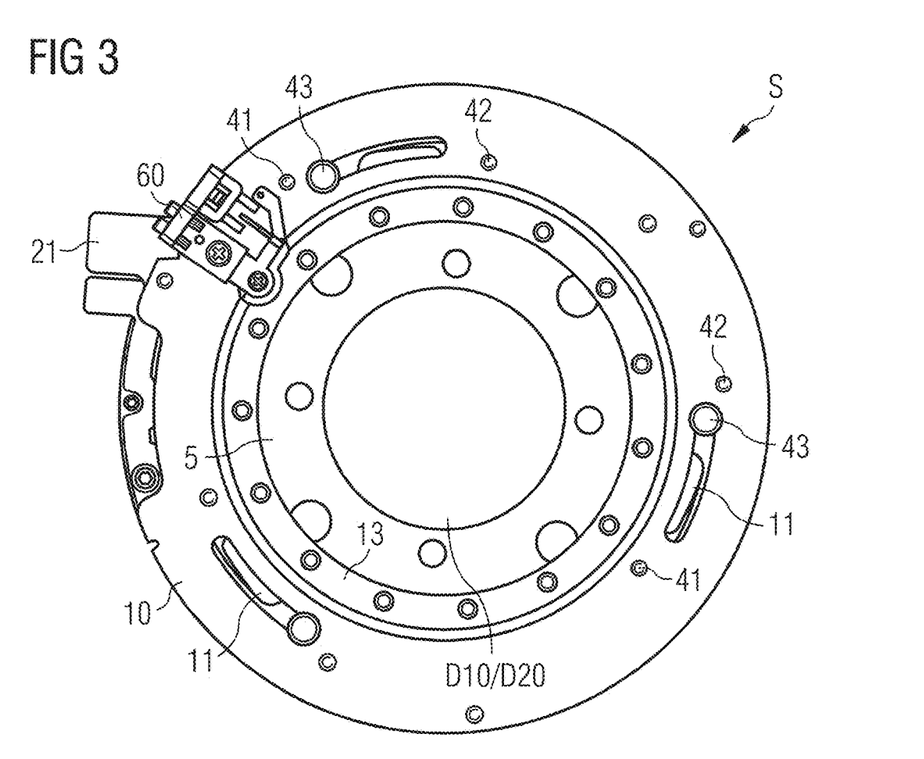
FIG. 3 shows a plan view of the interface module in accordance with FIG. 2, FIGS. 4 and 5 show plan views of the interface module in accordance with FIG. 2 with swivel elements in an open position or a clamping position.

FIG. 3 shows a plan view of the interface module in accordance with FIG. 2.

The interface module S serves to connect or fasten the collimator K to the X-ray generator R. The interface module S comprises a base plate 10, via which the interface module S is fastened to the collimator K. The base plate is here embodied as substantially round or circular. In its interior the base plate 10 forms a likewise round outlet opening D10 for the X-ray radiation. The outlet opening D10 is surrounded by a support area 13 for a flange 5 of the X-ray generator R, which is formed by a recess or annular depression in the base plate 10. The X-ray tube unit flange 5 encloses the X-ray outlet window of the X-ray generator R. The collar 7 of the X-ray tube unit flange 5 is attached to the support area for installation. In the installed state the collar 7 remains substantially attached to the support area 13.

The interface module S also comprises a round or circular adjustment plate 20, which is rotatably connected to the base plate 10 via a coupling mechanism. The adjustment plate 20 has a diameter substantially corresponding to the base plate 10. In its center the adjustment plate 20 also forms an outlet opening D20 for X-ray radiation. The base plate 10 and the adjustment plate 20 are in this respect embodied as annular. In the arrangement represented in accordance with FIG. 1 the adjustment plate 20 is arranged above the base plate 10, in other words closer to the X-ray generator R than the base plate 10. The outlet opening D20 of the adjustment plate 20 has a diameter which at least corresponds to the diameter of the X-ray tube unit flange 5, and is preferably embodied as larger than that of the X-ray tube unit flange 5. In this manner this can be guided through the outlet opening D20 to the support area 13 of the base plate 10 for installation.

Figure 4:
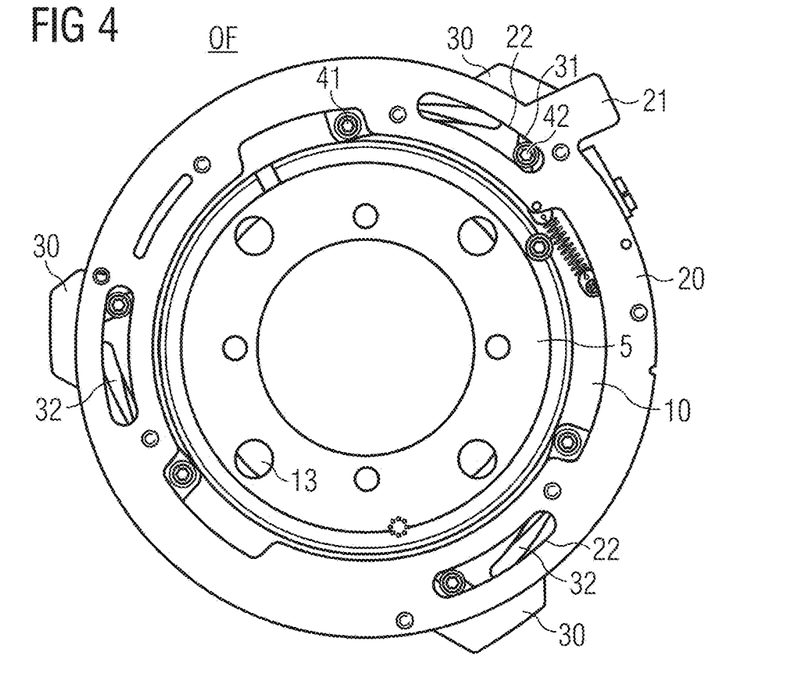
Figure 5:
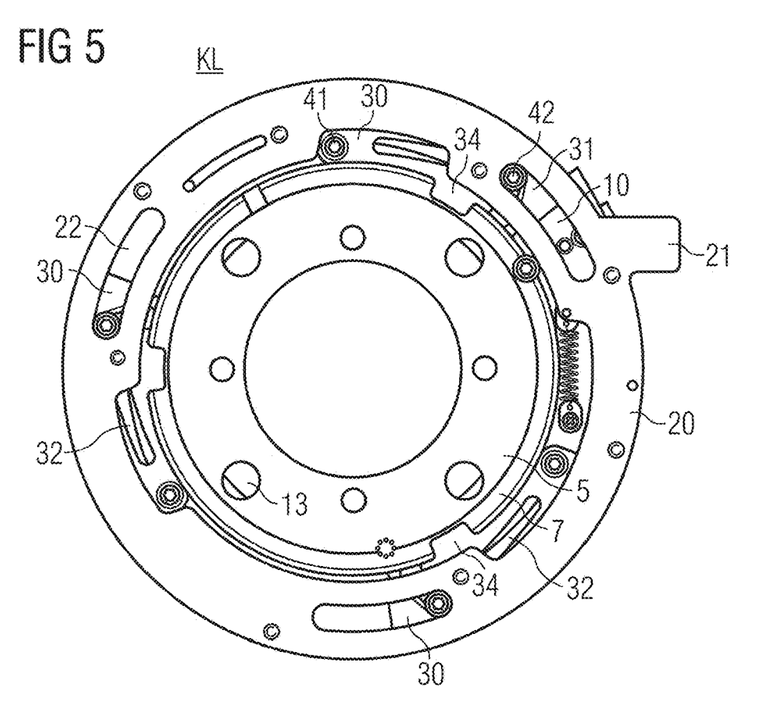

The interface module S also comprises at least one swivel element 30 which is movably connected to the base plate 10 and the adjustment plate 20 such that upon rotation of the adjustment plate 20 it pivots between a clamping position KL and an open position ÖF (cf. FIGS. 4 and 5). Specifically the interface module S in this embodiment comprises exactly three swivel elements 30, which are arranged at an angular spacing of 120° around the support area 13. The swivel elements 30 in this embodiment are arranged between the base plate and the adjustment plate 10, 20 and are likewise embodied as flat structures (cf. FIG. 6). In other embodiments more or fewer than three swivel elements can be provided. What is important is the uniformly distributed arrangement around the support area 13. In other embodiments the at least one swivel element 30 can also be arranged above the adjustment plate 20.

The adjustment plate 20 here has an adjustment lever 21 which extends outward substantially in the radial direction to the adjustment plate 20 and as a result can be readily accessed by an installer. On actuation of the adjustment lever 21 the adjustment plate 20 performs a revolution.

In other embodiments the adjustment plate 20 or the interface module S can comprise a motorized drive in order to rotate the adjustment plate 20.

The base plate 10, adjustment plate 20 and swivel elements 30 are connected to one another via a coupling mechanism, which is described in greater detail below.

The swivel elements 30 are each pivotably connected to the base plate via a first and a second coupling element 41, 42 firmly connected to the base plate. The coupling elements 41, 42 are here embodied as screws or bolts which are surrounded by sleeves and are screwed into the base plate 10 or otherwise anchored to it. The sleeves each permit a rotary motion about the respective coupling element 41, 42. The first coupling element 41 in each case penetrates a round, closed borehole 35 in the swivel element 30. The borehole 35 is in each case arranged at one end along a longitudinal axis of the swivel element 30. The swivel element 30 can therefore in each case rotate around the first coupling element 41. The second coupling element 42 in each case engages in a first slot 31 in the at least one swivel element 30 to guide a pivoting motion of the swivel element 30. The first slot 31 at least partially determines the pivot path of the swivel element 30. The first slot 31 runs along a curved track which is aligned substantially radially to the base plate 10 or perpendicular to the longitudinal axis of the swivel element 30. The first slot 31 is here embodied as open on one side. Alternatively it can also be embodied as completely closed.

Figure 6:
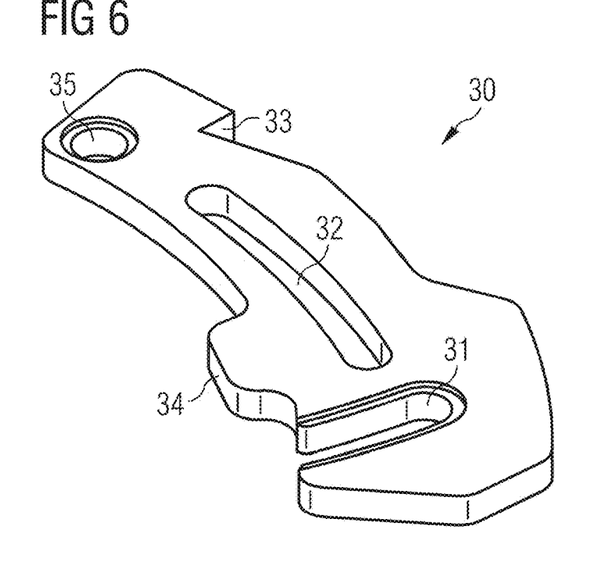
FIG. 6 shows a perspective view of a swivel element in an example embodiment of the present invention.

FIG. 6 shows, for better illustration, a perspective view of the at least one swivel element 30 in an example embodiment of the present invention.

In the embodiment shown here the second coupling element 42 in each case engages simultaneously in a slot 22 in the adjustment plate 20. The slot 22 in the adjustment plate 20 is provided here in order to create room for movement for the adjustment plate 20 in the case of a compact and in particular flat construction of the interface module S, which without the slot 22 would be obstructed by parts of the second coupling element 42. The slot 22 in the adjustment plate 20 runs substantially in the circumferential direction of the adjustment plate 20.

The adjustment plate 20 is furthermore rotatably connected to the base plate 10 via at least one third coupling element 43. The third coupling element 43 is embodied similarly to the first or second coupling element 41, 42, wherein the anchoring here takes place in the adjustment plate 20. The third coupling element 43 in each case serves to guide the rotary motion of the adjustment plate 20. For this purpose the third coupling element 43 in each case engages in a slot 11 in the base plate 10. The slot 11 in the base plate 10 runs substantially in the circumferential direction of the base plate 10. The length of the slot 11 defines a maximum and a minimum deflection of the adjustment plate 20 in respect of the base plate 10.

The third coupling element 43 in each case penetrates a second slot 32 in the swivel element 30 to guide the pivoting motion of the swivel element 30. The second slot 32 in the swivel element 30 likewise runs along a curved track and is substantially aligned to the longitudinal axis of the swivel element 30. It is arranged between the borehole 35 and the first slot 31. The third coupling element 43 in each case forces a pivoting motion of the associated swivel element 30 by its engagement in the second slot 32, as soon as the adjustment plate 20 is rotated relative to the base plate 10.

The pivoting motion moves the swivel element 30 between an open position ÖF and a clamping position KL.

FIGS. 4 and 5 show plan views of the interface module S in accordance with FIG. 2 with swivel elements 30 in the open position ÖF or the KL clamping position. The open position ÖF is characterized in that the at least one swivel element 30 is arranged outside the support area 13 for the X-ray tube unit flange 5. In other words, the swivel element 30 does not project into the support area 13 or project over it. The swivel element 30 consequently exposes the outlet opening D20 in the adjustment plate 20 for the insertion or removal of the X-ray tube unit flange 5. The interface module is open.

In contrast, the clamping position KL is characterized in that the at least one swivel element 30 projects at least partially over the support area 13. In particular, a clamping area 34 of the swivel element 30 in the clamping position KL engages behind the collar 7 of the X-ray tube unit flange 5 and presses it against the support area 13. The interface module S is closed or obstructed and the X-ray tube unit flange 5 is fixed.

The position and length of the at least one slot 11 in the base plate 10 are selected such that with minimal deflection of the adjustment plate 20, in other words the initial position of the adjustment plate 20 corresponding to the open position ÖF (FIG. 4), the third coupling element 43 penetrates the second slot 32 in the swivel element 30 at its end facing the first coupling element 41. The swivel element 30 lies completely outside the support area 13. At maximum deflection of the adjustment plate 20 in accordance with the clamping position KL, the third coupling element 43 penetrates the second slot 32 of the swivel element 30 at its end facing the second coupling element 42. During the pivoting motion the swivel element 30 is drawn at least partially, in particular by its clamping area 34, into or over the support area 13.

Figure 7:
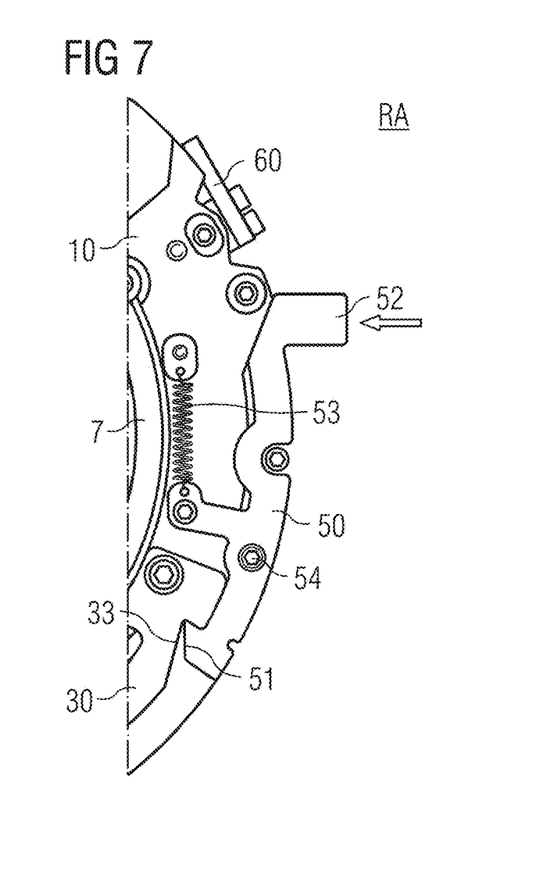
FIGS. 7 and 8 show detailed views of a securing device in accordance with the interface module from FIG. 2.
Figure 8:
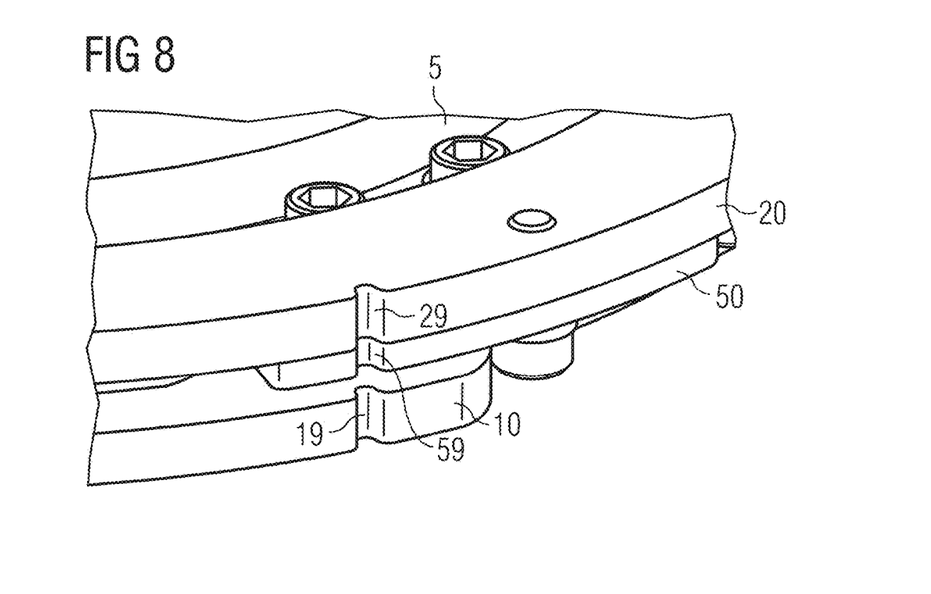

FIGS. 7 and 8 show detailed views of a securing device 50 in accordance with the interface module S from FIG. 2.

The securing device 50 serves to fix at least one swivel element 30 in the clamping position KL. Thus the securing device prevents any inadvertent opening of the interface module S. In this embodiment the securing device 50 is arranged in the plane of the at least one swivel element 30, in other words between the base plate 10 and the adjustment plate 20. The securing device 50 is rotatably connected to the adjustment plate 10 via a bolt 54. It comprises a latching hook 51, which under spring force adopts a latching position (RA) in a latching groove 33 of the at least one swivel element 30, when the swivel element 30 adopts the clamping position KL. The spiral spring 53 is here fixed on one side to the adjustment plate 30 and on its other side is connected to the securing device 50. The spring 53 is connected to the securing device 50 such that it brings about a torque which draws the securing device here in a clockwise direction around the bolt 54. As soon as the latching hook 51 reaches the latching groove 33 thanks to a rotary motion of the adjustment plate 20 from the minimum deflection to the maximum deflection, the latching hook 51 adopts the latching position RA thanks to the effect of the torque and engages in the latching groove 33. In this manner the clamping position KL of the interface module S is secured. In order to undo the securing part again, for example for disassembly of the collimator K, the securing device 50 comprises a pressure lever 52, which can be pressed into the interface module S, causing an opposing force counteracting the spring tensioning force and drawing the latching hook 51 out of the latching groove 33 and releasing a rotation of the adjustment plate 20 in the direction of minimum deflection.

In alternative embodiments the securing device itself can be embodied as bendable, at least in subregions, and in this manner can apply the adjustment force for the latching hook.

In the embodiment shown here (cf. FIG. 8) the securing device 50 also comprises a first control notch 59, which lies congruent to at least one second control notch 29, 19 of the adjustment plate 20 and/or the base plate 10, when the latching hook 51 adopts the latching position RA. If the at least one swivel element 30 is not in the clamping position KL, the at least two control notches do not lie congruent to one another. In this respect a simple visual check of the clamping position KL is enabled. Particularly advantageously, the control notches 59, 19, 29 are color-coded, which further simplifies the visual check.

Figure 9:
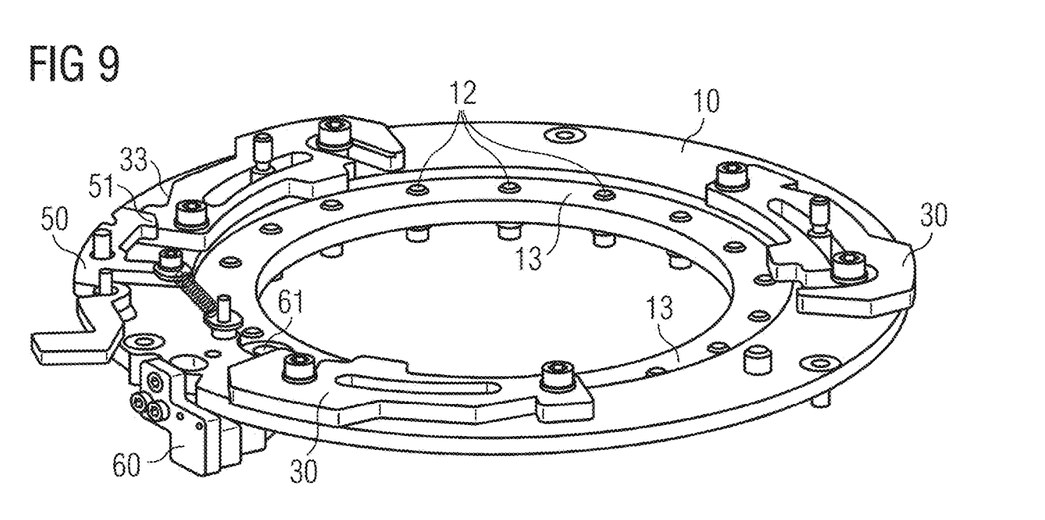
FIG. 9 shows a detailed view of the interface module in accordance with FIG. 2.

FIG. 9 shows a detailed view of the interface module S in accordance with FIG. 2. The support area 13 for the X-ray tube unit flange 5 here comprises a plurality of spring-loaded pressure pieces 12. Thanks to a spring force acting on the pressure pieces these project out of the support area 13, act on the adjacent X-ray tube unit flange 5 and press it against the at least one swivel element 30 in the clamping position KL. In this manner a uniform force effect and clamping effect is exerted on the X-ray tube unit flange 5 even in the case in particular of manufacturing-related inaccuracies in components, and a stable—in particular stable against tipping—connection of the collimator K to the X-ray generator R is achieved.

The example embodiment shown here also comprises an adjustment device 60 comprising a spring-loaded pressure element 61 and is described more fully with reference to the following figures.

Figure 10:
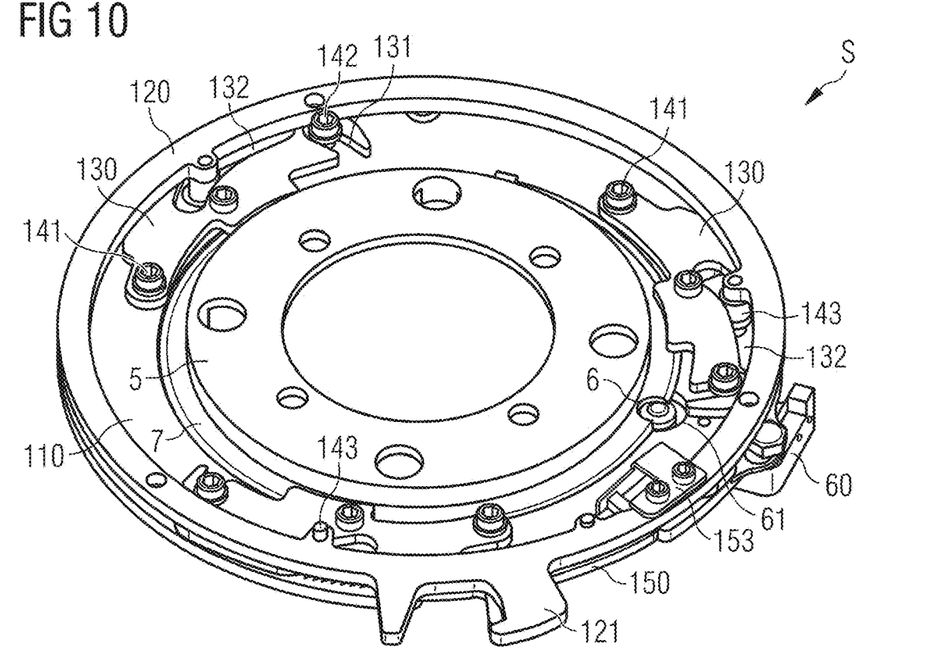
FIG. 10 shows a perspective view of an interface module in another example embodiment of the present invention.

FIG. 10 shows a perspective view of an interface module S in another example embodiment of the present invention.

Figure 11:
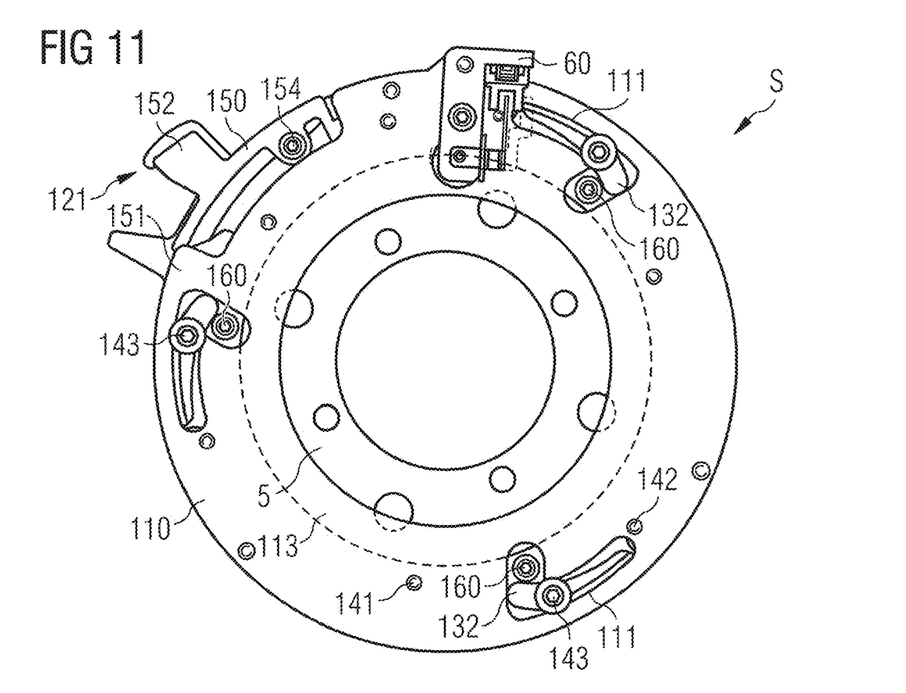
FIG. 11 shows a plan view of the interface module in accordance with FIG. 10.

FIG. 11 shows a plan view of the interface module S in accordance with FIG. 10.

The interface module S comprises a base plate 110, via which the interface module S is fastened to the collimator K. Here too, the base plate is embodied as substantially round. In its interior the base plate 110 forms a likewise round outlet opening for X-ray radiation. The base plate 110 likewise forms a support area 113 for the flange 5 of the X-ray generator R. The collar 7 of the X-ray tube unit flange 5 is attached to the support area for installation. In the installed state the collar 7 remains substantially attached to the support area 113.

The interface module S here also comprises a round adjustment plate 120, which is rotatably connected to the base plate 110 via a coupling mechanism. The adjustment plate 120 has a diameter substantially corresponding to the base plate 110. The adjustment plate 120 too in its center forms an outlet opening for X-ray radiation. The adjustment plate 120 too is arranged above the base plate 110 in the arrangement represented in accordance with FIG. 1, in other words closer to the X-ray generator R than the base plate 110. The outlet opening in the adjustment plate 20 has a diameter which at least corresponds to the diameter of the X-ray tube unit flange 5.

The interface module S comprises three swivel elements 130, which are movably connected to the base plate 110 and adjustment plate 120 such that they pivot when the adjustment plate 120 rotates between a clamping position KL and an open position ÖF. FIGS. 10 and 11 each show the clamping position of the swivel elements 130. The swivel elements 130 are also arranged between the base plate and the adjustment plate 110, 120 in this embodiment.

The adjustment plate 120 here has an adjustment lever 121, which extends radially outward and comprises two engagement elements. This facilitates a manual adjustment in both directions of rotation.

The coupling mechanism between the base plate 110, the adjustment plate 120 and the three swivel elements 130 is described in greater detail below.

The swivel elements 130 are each pivotably connected to the base plate via a first coupling element 141 and a second coupling element 142 firmly connected to the base plate. The coupling elements 141, 142 are embodied as described with reference to FIGS. 2 and 3. Alternative embodiments are likewise conceivable. The first coupling element 141 in each case penetrates a round, closed borehole 135 in the swivel elements 130. The borehole 135 is in each case arranged at an end along a longitudinal axis of the swivel element 130. The swivel element 130 can therefore in each case rotate around the first coupling element 141. The second coupling element 142 in each case engages in a first slot 131 in the at least one swivel element 131 to guide a pivoting motion of the swivel element 130. The first slot 131 at least partially determines the pivot path of the swivel element 130. The first slot 131 runs along a curved track, which is aligned substantially radially to the base plate 110 or perpendicular to the longitudinal axis of the swivel element 130. Here too, the first slot 131 is embodied as open on one side.

Figure 12:
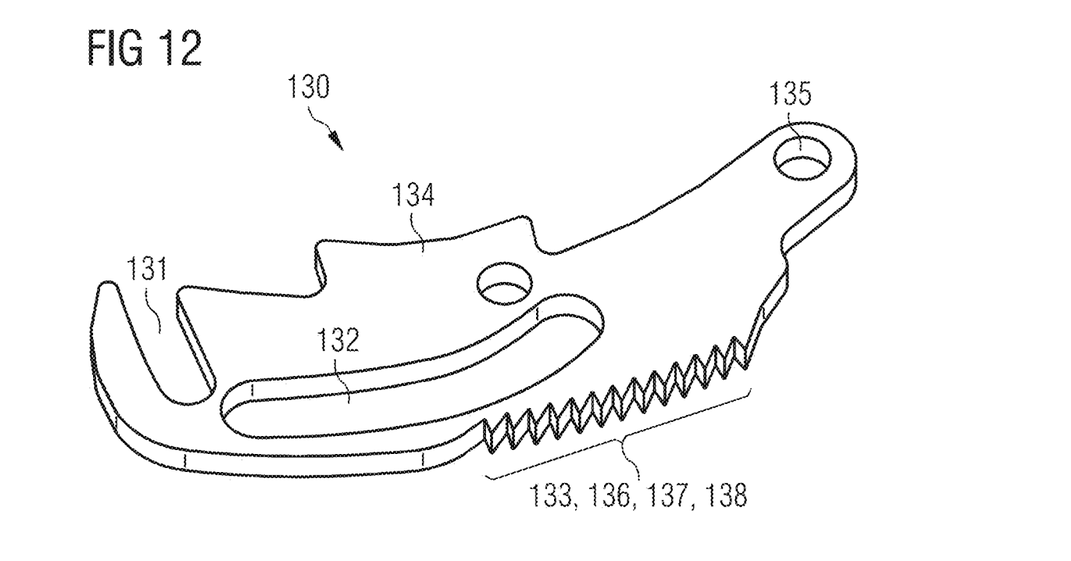
FIG. 12 shows a perspective view of a swivel element in a further example embodiment of the present invention.

FIG. 12 shows, for better illustration, a perspective view of the at least one swivel element 130 in an example embodiment of the present invention.

The adjustment plate 120 is furthermore rotatably connected to the base plate 110 via at least one third coupling element 143, here specifically three. The third coupling element 143 is embodied similarly to the first or second coupling element 141, 142, wherein the anchoring takes place here in the adjustment plate 120. The third coupling element 143 in each case serves to guide the rotary motion of the adjustment plate 120. For this purpose the third coupling element 143 in each case engages in a slot 111 in the base plate 110. The slot 111 in the base plate 110 runs substantially in the circumferential direction of the base plate 110. The length of the slot 111 defines a maximum and a minimum deflection of the adjustment plate 120 in respect of the base plate 110.

The third coupling element 143 in each case penetrates a second slot 132 in the swivel element 130 to guide the pivoting motion of the swivel element 130. The second slot 132 in the swivel element 130 likewise runs along a curved track and is substantially aligned to the longitudinal axis of the swivel element 130. It is arranged between the borehole 135 and the first slot 131. The third coupling element 143 in each case forces a pivoting motion of the associated swivel element 130 by its engagement in the second slot 132, as soon as the adjustment plate 120 is rotated relative to the base plate 110.

The pivoting motion moves the swivel element 130 between an open position ÖF and a clamping position KL. The opening and clamping position ÖF, KL correspond substantially to the positions described with reference to FIGS. 4 and 5. In particular, a clamping area 134 of the control element 130 in the open position ÖF lies outside the support area 111 of the base plate 110. The clamping areas 134 project over the support area 111 and engage behind an X-ray tube unit flange collar 7 arranged on the support area 111 in the clamping position KL.

FIG. 10 and FIG. 11 also show a securing device 150. The securing device 150 also serves to fix at least one swivel element 130 in the clamping position KL. The securing device 150 is arranged in the plane of the at least one swivel element 130, in other words between the base plate 110 and the adjustment plate 120. The securing device 150 is rotatably connected to the adjustment plate 110 via bolt 154. It comprises a latching hook 151, which under spring force adopts a latching position (RA) in one of a plurality of latching grooves 133, 136, 137, 138, shown by way of example, in the at least one swivel element 130, when the swivel element 30 adopts one of a plurality of clamping positions KL possible here. The various clamping positions KL each correspond to another clamping effect or pressing force which is exerted on the X-ray tube unit flange collar 7. The clamping effect is brought about in this embodiment via a 45° chamfer 135 of the clamping area 134, which comes more and more in contact with a corresponding 45° chamfer of the X-ray tube unit flange collar 7 and presses the flange onto the support area 111 when the adjustment plate 120 is rotated further in the direction of maximum deflection. As a result, a desired pressing force can advantageously be set.

Figure 13:
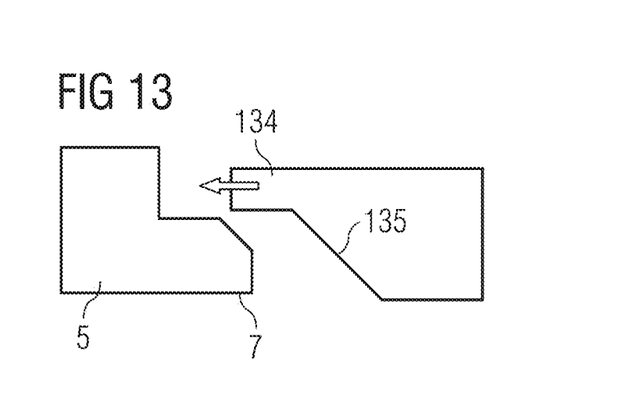
FIG. 13 shows a further detailed view of the interface module in accordance with FIG. 10.

FIG. 13 shows a further detailed view of the interface module S in accordance with FIG. 10, which better illustrates the described 45° chamfer.

The spring force is in this embodiment applied by a spring steel sheet 153 which is fixed to the adjustment plate 120 and upon rotation of the securing device 150 is deflected through this. As soon as the latching hook 151 reaches the first of the latching grooves 133, 136, 137, 138 as a result of a rotary motion of the adjustment plate 120 from the minimum deflection to the maximum deflection, the latching hook 151 adopts the latching position RA thanks to the torque effect and engages in the first latching groove. In this manner a first clamping position is secured corresponding to a minimum clamping effect of the interface module S. If the adjustment plate 120 is twisted further in the direction of maximum deflection, the latching hook moves along the latching grooves until the maximum deflection of the adjustment plate 120 or the last of the latching grooves corresponding to a clamping position with the greatest clamping effect is reached. In order to undo the securing part again, the securing device 150 here too comprises a pressure lever 152, which can be pressed into the interface module S, causing an opposing force counteracting the spring tensioning force and drawing the latching hook 51 out of the latching grooves 133, 136, 137, 138.

FIG. 11 shows an alternative configuration of the 45° chamfer. Here each swivel element 130 comprises a sliding element 160 which is arranged on the clamping area 134 and is shaped precisely to the X-ray tube unit flange chamfer. The sliding element can for example be embodied as round or in the shape of a block or cube. The sliding element 160 can be embodied as a rotating part, press part or cast part and is fixed to the clamping area, for example screwed, riveted, pressed or bonded in the clamping area by a borehole.

In alternative embodiments an adjustable clamping effect can be achieved, in that the coupling mechanism is fitted with a spring system between the swivel element 130 and the adjustment plate 120. By spring force the spring system brings about a radial pressing force, which presses the 45° chamfer of the clamping area onto the 45° chamfer of the X-ray tube unit flange 5.

FIGS. 10 and 11 also show an adjustment device 60 for fine-tuning an angular position between the collimator and the X-ray generator, wherein the adjustment device 60 comprises a spring-loaded pressure element 61 which engages into a recess 6 of the X-ray tube unit flange 5 through the support area to define the angular position in a 0° position. During the installation the collimator is aligned prior to fixing by the interface module S in the 0° position relative to the X-ray generator R, in other words in an initial position. The pressure element 61 and recess 6 in the flange 5 and a corresponding recess in the base area serve to find this 0° position. If the pressure element latches into the recesses, the 0° position is typically reached. However, because of manufacturing faults in the individual components it may be the case that the desired initial position cannot be adopted. For this purpose the adjustment device 60 also comprises an adjusting device 62 for setting the 0° position. The adjusting device 62 here comprises a slot running circumferentially to the adjustment plate and a screw, via which the location of the base plate relative to the X-ray tube unit flange can be set. Using the adjusting device the angular position of the pressure element relative to the recess 6 can in this manner be adjusted by +/−1° and the 0° position can be reached despite the variations in components.

The pressure element 61 of the adjustment device 60 enables the angular position of both components to be adjusted to one another during operation of the X-ray generator R and the collimator. A user can, by overcoming a defined torque which he or she applies to the collimator K, adjust the collimator out of the 0° position into any other angular position. In the desired angular position the pressure element 61 brings about a sufficient tightening force on the X-ray tube unit flange 5.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

Where it is not explicitly stated but is nevertheless expedient and within the meaning of the present invention, individual example embodiments, individual subsidiary aspects thereof or features can be combined or exchanged with one another, without departing from the framework of the present invention. Advantages of the present invention described with reference to an example embodiment also, where transferable, apply to other example embodiments without being explicitly mentioned.

What is claimed is:

1. An interface module to connect a collimator to an X-ray generator, the interface module comprising:
    a base plate, which forms a support area for an X-ray tube unit flange of the X-ray generator;
    an adjustment plate, which is rotatably connected to the base plate; and
    at least one swivel element movably connected to the base plate and the adjustment plate such that, upon rotation of the adjustment plate, the at least one swivel element pivots between a clamping position and an open position.

2. The interface module as claimed in claim 1, wherein the at least one swivel element comprises three swivel elements, which are arranged at an angular spacing of 120° around the support area.

3. The interface module as claimed in claim 2, wherein the adjustment plate comprises an adjustment lever that, when actuated, causes the adjustment plate to rotate.

4. The interface module as claimed in claim 2, wherein, in the open position, the at least one swivel element is arranged outside the support area for the X-ray tube unit flange.

5. The interface module as claimed in claim 2, wherein the at least one swivel element is pivotably connected to the base plate via at least one first coupling element and at least one second coupling element firmly connected to the base plate, and wherein the at least one second coupling element is configured to engage in a first slot in the at least one swivel element to guide a pivoting motion of the at least one swivel element.

6. The interface module as claimed in claim 1, wherein the adjustment plate comprises an adjustment lever that, when actuated, causes the adjustment plate to rotate.

7. The interface module as claimed in claim 1, wherein the adjustment plate comprises a motorized drive to rotate the adjustment plate.

8. The interface module as claimed in claim 1, wherein, in the open position, the at least one swivel element is arranged outside the support area for the X-ray tube unit flange.

9. The interface module as claimed in claim 1, wherein, in the clamping position, the at least one swivel element is configured to project at least partially over the support area.

10. The interface module as claimed in claim 1, wherein the at least one swivel element is pivotably connected to the base plate via at least one first coupling element and at least one second coupling element firmly connected to the base plate, and wherein the at least one second coupling element is configured to engage in a first slot in the at least one swivel element to guide a pivoting motion of the at least one swivel element.

11. The interface module as claimed in claim 10, wherein the at least one second coupling element is configured to engage in a slot in the adjustment plate.

12. The interface module as claimed in claim 1, wherein the adjustment plate is rotatably connected to the base plate via at least one coupling element, and wherein the at least one coupling element, in each case, is configured to engage in a slot in the base plate to guide rotary motion of the adjustment plate.

13. The interface module as claimed in claim 12, wherein the at least one coupling element is configured to simultaneously penetrate a second slot in the at least one swivel element to guide a pivoting motion of the at least one swivel element.

14. The interface module as claimed in claim 1, further comprising:
   a securing device configured to fix the at least one swivel element in the clamping position.

15. The interface module as claimed in claim 14, wherein the securing device is rotatably or bendably connected to the adjustment plate and includes a latching hook, which under spring force, adopts a latching position in a latching groove in the at least one swivel element, when the at least one swivel element adopts the clamping position.

16. The interface module as claimed in claim 15, wherein the at least one swivel element has a clamping area with a chamfer and a plurality of latching grooves.

17. The interface module as claimed in claim 14, wherein the securing device comprises:
   a first control notch, which lies congruent to at least one second control notch in at least one of the adjustment plate or the base plate, when a latching hook adopts a latching position.

18. The interface module as claimed in claim 1, wherein the support area comprises:
   at least one spring-loaded pressure device for the X-ray tube unit flange, the at least one spring-loaded pressure device configured to press the X-ray tube unit flange against the at least one swivel element in the clamping position.

19. The interface module as claimed in claim 1, further comprising:
   an adjustment device configured to fine-tune an angular position between the collimator and the X-ray generator, the adjustment device including a spring-loaded pressure element and an adjusting device, the spring-loaded pressure element configured to engage in a recess in the X-ray tube unit flange through the support area to define the angular position in a 0° position, and the adjusting device configured to set the 0° position.

20. A collimator for collimation of X-ray radiation, the collimator comprising an interface module as claimed in claim 1.

* * * * *